United States Patent [19]
Cheng et al.

[11] Patent Number: 5,770,615
[45] Date of Patent: Jun. 23, 1998

[54] CATECHOLAMINE SURROGATES USEFUL AS $\beta_3$ AGONISTS

[75] Inventors: Peter T. W. Cheng, Lawrenceville; Gregory S. Bisacchi, Ringoes; Ashvinikumar V. Gavai, Plainsboro; Kathleen M. Poss, Lawrenceville; Denis E. Ryono, Princeton; Philip M. Sher, Plainsboro; Chong-qing Sun, East Windsor; William N. Washburn, Titusville, all of N.J.

[73] Assignee: Bristol-Myers Squibb Company, Princeton, N.J.

[21] Appl. No.: 825,309

[22] Filed: Mar. 28, 1997

Related U.S. Application Data

[60] Provisional application No. 60/014,861 Apr. 4, 1996.

[51] Int. Cl.[6] .................. A61K 31/425; A61K 31/165; C07D 277/28; C07C 321/00
[52] U.S. Cl. .................. 514/365; 514/374; 514/618; 514/619; 514/620; 548/204; 548/236; 564/162; 564/163; 564/164; 564/165
[58] Field of Search .................. 564/162, 163, 564/164, 165; 514/618, 619, 620, 365, 374; 548/204, 236

[56] References Cited

U.S. PATENT DOCUMENTS

| | | | |
|---|---|---|---|
| 3,341,584 | 9/1967 | Larsen et al. | 562/114 |
| 3,574,741 | 4/1971 | Gould et al. | 564/99 |
| 3,660,487 | 5/1972 | Larsen et al. | 562/84 |
| 3,689,524 | 9/1972 | Jack et al. | 560/42 |
| 3,705,233 | 12/1972 | Lunts et al. | 514/653 |
| 3,732,300 | 5/1973 | Lunts et al. | 564/165 |
| 3,803,230 | 4/1974 | Jack et al. | 564/165 |
| 3,804,899 | 4/1974 | Ebnother et al. | 564/361 |
| 3,906,110 | 9/1975 | Francis | 514/653 |
| 3,954,871 | 5/1976 | Buu-Hoi et al. | 564/363 |
| 4,012,444 | 3/1977 | Lunts et al. | 564/165 |
| 4,035,512 | 7/1977 | Sugihara et al. | 514/654 |
| 4,066,755 | 1/1978 | Lunts et al. | 514/166 |
| 4,338,333 | 7/1982 | Ainsworth et al. | 514/539 |
| 4,638,070 | 1/1987 | Lambelin et al. | 549/23 |
| 4,707,497 | 11/1987 | Cecchi et al. | 514/647 |
| 4,772,631 | 9/1988 | Holloway et al. | 514/539 |
| 5,061,727 | 10/1991 | Bloom et al. | 514/465 |

FOREIGN PATENT DOCUMENTS

| | | |
|---|---|---|
| A-192231/83 | 3/1984 | Australia . |
| 1204445 | 6/1983 | Canada . |
| 0 023 385 | 2/1981 | European Pat. Off. . |
| 556880 | 9/1993 | European Pat. Off. . |
| 122967 | 10/1975 | German Dem. Rep. . |
| 2310142 | 3/1973 | Germany . |
| 51125291 | 12/1974 | Japan . |
| 51-143678 | 6/1975 | Japan . |
| 51-149282 | 6/1975 | Japan . |
| 53002443 | 6/1976 | Japan . |
| 837012 | 4/1993 | South Africa . |
| 1005025 | 9/1965 | United Kingdom . |
| 1367678 | 9/1974 | United Kingdom . |

OTHER PUBLICATIONS

Washburn et al, Preparation of hydroxyamino ethylphenyl-sulfonamide catecholamine surrogates useful as beta–3–adrenergic agonists, CA 95:938107, (1995).

*Primary Examiner*—Deborah C. Lambkin
*Attorney, Agent, or Firm*—Burton Rodney

[57] ABSTRACT

Compounds of the formula

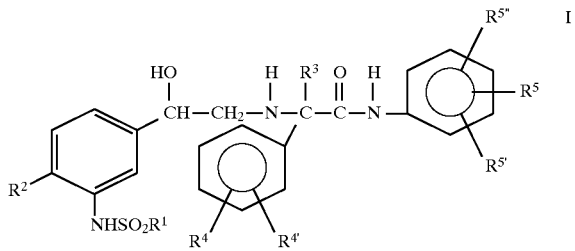

and pharmaceutically acceptable salts thereof.

These compounds are beta three adrenergic receptor agonists and are useful, therefore for example, in the treatment of diabetes, obesity and gastrointestinal diseases.

23 Claims, No Drawings

CATECHOLAMINE SURROGATES USEFUL AS β₃ AGONISTS

Provisional Application No. 60/014,861, Apr. 4, 1996.

BRIEF DESCRIPTION OF THE INVENTION

The present invention is directed to compounds of the formula

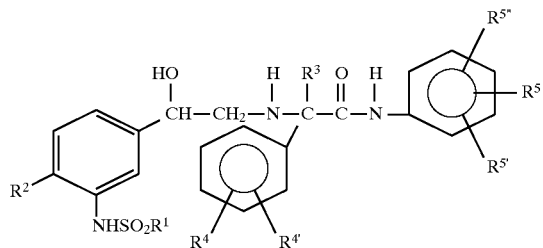

and pharmaceutically acceptable salts thereof As used in formula I, and throughout the specification, the symbols have the following meanings:

$R^1$ is lower alkyl, aryl or arylalkyl;

$R^2$ is hydrogen, hydroxyl, hydroxymethyl or halogen;

$R^3$ is hydrogen or alkyl;

$R^4$ and $R^{4'}$ are independently hydrogen, alkoxy, alkoxymethyl, hydroxyl, —CN, —CON($R^6$)$R^{6'}$, —CO$_2R^6$, —N($R^6$)$R^{6'}$, —NR$^6$COR$^8$, —NR$^6$SO$_2R^1$; or $R^4$ and $R^{4'}$ may together with the carbon atoms to which they are bonded form a heterocycle;

$R^5$, $R^{5'}$ and $R^{5''}$ are independently A or B, wherein A is hydrogen, alkyl, cycloalkyl, halogen, hydroxyl, aryl, alkoxy, cyano, —SR$^7$, —SOR$^7$, —SO$_2R^7$, —N($R^6$)$R^{6'}$, —NR$^6$COR$^8$, —OCH$_2$CON($R^6$)$R^{6'}$, —OCH$_2$CO$_2R^6$, CON($R^6$)$R^{6'}$, —CO$_2R^6$; and B is —(CH$_2$)$_n$N($R^6$)$R^{6'}$, —(CH$_2$)$_m$PO(OR$^6$)OR$^{6'}$, —(CH$_2$)$_n$NR$^6$COR$^8$, —O-aryl, —OCH$_2$CH$_2$N($R^6$)$R^{6'}$, —COR$^7$, —SO$_2$N($R^6$)$R^{6'}$, —NR$^6$CO$_2R^7$, —NR$^6$CO(N($R^6$)$R^{6'}$), heterocycle or —R$^5$ and $R^{5'}$ may together with the carbon atoms to which they are bonded form a heterocycle; provided that at least one of $R^5$, $R^{5'}$ and $R^{5''}$ is B;

$R^6$ and $R^{6'}$ are independently hydrogen or lower alkyl;

$R^7$ is lower alkyl;

$R^8$ is hydrogen, lower alkyl, aryl or arylalkyl;

m is an integer of 0 to 6; and n is an integer of 1 to 6.

The compounds of formula I possess activity at the beta three adrenergic receptor in mammals and are useful in the treatment of diabetes, obesity, and intestinal hypermotility disorders.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to optionally substituted, straight and branched chain saturated hydrocarbon groups having 1 to 12 carbon atoms. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include one or more of the following groups: halo (such as CCl$_3$ or CF$_3$), aryl, alkylaryl, haloaryl, cycloalkyl, (cycloalkyl)alkyl, hydroxyl, alkylamino, thiol, alkylthio or Y substituents where Y is —CN, alkoxy, —CON($R^6$)$R^{6'}$, —CO$_2R^7$, —N($R^6$)$R^{6'}$, —PO(OR$^6$)OR$^{6'}$, —NR$^6$COR$^8$, or —N($R^6$)SO$_2R^1$.

The term "lower alkyl" as employed herein includes such alkyl groups as described above containing 1 to 6 carbon atoms.

The term "alkoxy" refers to any of the above alkyl groups linked to an oxygen atom.

The term "lower alkoxy" refers to any of the above lower alkyl groups linked to an oxygen atom.

The term "aryl" refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, halogens or 1, 2 or 3 lower alkoxy groups. Phenyl and substituted phenyl are preferred.

The term "halogen" or "halo" refers to chlorine, bromine, fluorine or iodine.

The term "heterocycle" refers to fully saturated or unsaturated rings of 5 or 6 atoms containing one or two oxygen and/or sulfur atoms and/or one to four nitrogen atoms provided that the total number of hetero atoms in the ring is four or less. The hetero ring is attached by way of an available atom. Preferred monocyclic heterocycle groups include 2- and 3-thienyl, 2-thiazole, 2-oxazole, 2- and 3-furyl, 2-, 3- and 4-pyridyl and imidazolyl. The term heterocycle also includes bicyclic rings wherein the five- or six-membered ring containing oxygen and/or sulfur and/or nitrogen atoms as defined above is fused to a benzene ring and the bicyclic ring is attached by way of an available carbon atom. Preferred bicyclic heterocycle groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl, 4-, 5-, 6- or 7-benzofuranzanyl, 4-, 5-, 6- or 7-benzodioxolyl and 4-, 5-, 6- or 7-benzofuryl. The term "heterocycle" also includes such monocyclic and bicyclic rings wherein an available carbon atom is substituted with a (C$_1$–C$_4$)-alkyl, aryl, (C$_1$–C$_4$)-alkylthio, (C$_1$–C$_4$)-alkoxy, halo, nitro, keto, cyano, hydroxyl, azo, thiazo, amino, —NH—(C$_1$–C$_4$)-alkyl, —N((C$_1$–C$_4$)-alkyl)$_2$, —CF$_3$ or —OCHF$_2$ or such monocyclic and bicyclic rings wherein two or three available carbons have substituents selected from hydroxyl, methylmethoxy, methylthio, halo, —CF$_3$, nitro, amino and —OCHF$_2$.

The compounds of formula I can be converted to salts, in particular pharmaceutically acceptable salts using procedures known to one of ordinary skill in the art. If the compounds of formula I have at least one basic center, they can form acid addition salts. These are formed, for example, with strong mineral acids, such as sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane- (of 1 to 4 carbon atoms) or arylsulfonic acids, for example methane- or p-toluenesulfonic acid. Corresponding acid addition salts can also be formed having, if desired, an additionally present basic center. The compounds of formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form.

It should be understood that the present invention includes prodrug forms of the compounds of formula I.

The compounds of the instant invention may be in the free or hydrate form, and may be obtained by methods exemplified by the following descriptions.

Compounds of formula I can be prepared by coupling a compound having the formula

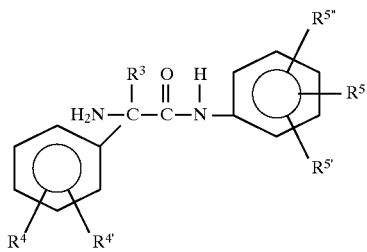

with compound of formula

optionally in the presence of an acid scavenger such as diisopropylethylamine to form a compound of formula

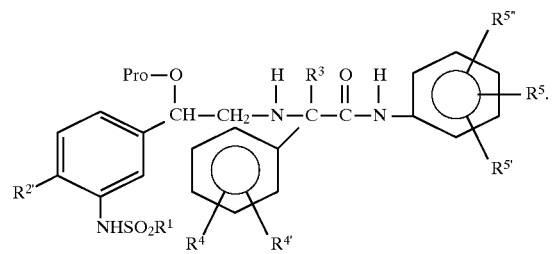

In formula III and/or IV and throughout the specification, Pro is a suitable protecting group such as triethylsilyl or t-butyldimethylsilyl; $R^{2'}$ is hydrogen, hydroxyl, halogen, $-CO_2R^7$, $-CH_2OPro'$, or $-O-Pro'$ where Pro' is a suitable protecting group such as benzyl or t-butyldimethylsilyl; and L is a leaving group such as iodide, bromide, p-toluene sulfonate, mesylate or trifluoromethane sulfate.

Compounds of formula IV, where Pro is triethylsilyl or t-butyldimethylsilyl are then sequentially deprotected to form compounds of formula I by first treatment with a source of fluoride such as tetrabutylammonium fluoride in a solvent such as tetrahydrofuran or ammonium fluoride in a solvent such as methanol to remove the Pro moiety; and where $R^{2'}$ is O-benzyl, hydrogenolysis in a solvent such as methanol using a catalyst such as Pd or Raney nickel or alternatively treatment with a Lewis acid such as $BBr_3$ in a solvent such as methylene chloride to remove the O-benzyl group; and where $R^{2'}$ is $-CO_2R^7$, reduction with a reducing agent such as lithium borohydride in a solvent such as tetrahydrofuran to generate compounds of formula I where $R^2$ is $-CH_2OH$.

Alternatively, compounds of formula IV may be prepared by initially coupling compounds of formula

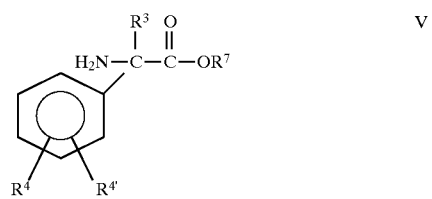

with compounds of formula III to generate compounds of formula

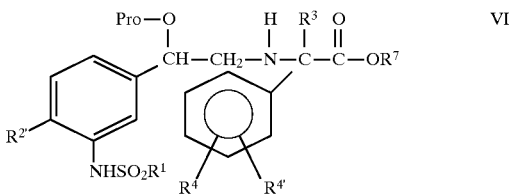

where $R^{2'}$ is not hydroxyl or $CO_2R^7$ followed by careful hydrolysis using a base such as lithium hydroxide in a solvent such as tetrahydrofuran/methanol/water to generate compounds of formula

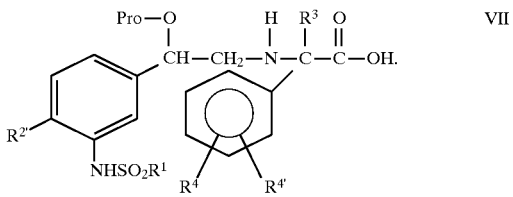

Subsequently compounds of formula VII are condensed with an appropriate aniline using standard protocols for derivatization of amino acids to generate compounds of formula IV.

A preferred method entails pretreatment of VII in a solvent mixture such as 1,2-dichloroethane/ dimethylformamide with 1-hydroxy-7-azabenztriazole and a water soluble carbodiimide at 0° C. prior to reaction with the appropriate aniline. In some instances for compounds of formula VII where $R^{2'}$ is O-Pro', it is preferable to deprotect the phenol prior to condensation with the aniline.

Alternatively, compounds of formula I may be prepared by stirring two equivalents of a compound of formula II with one equivalent of a compound of formula

(VIII)

where L' is a leaving group such as bromide, iodide or chloride and $R^{2''}$ is hydrogen, hydroxyl, halogen, —$CO_2R^7$, or O-benzyl, to form compounds of formula

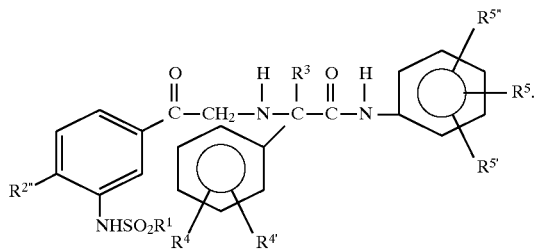

(IX)

Compounds of formula IX are then converted to compounds of formula I by sequential treatment with a reducing agent such as sodium borohydride (and in the case where $R^{2''}$ is O-benzyl, subsequent hydrogenolysis using a catalyst such as Pd or Raney nickel to remove the O-benzyl group) in a solvent such as methanol; and where $R^{2''}$ is —$CO_2R^7$, reduction with a reducing agent such as lithium borohydride in a solvent such as tetrahydrofuran to generate compounds of formula I where $R^2$ is —$CH_2OH$.

Compounds of formula II where $R^3$ is hydrogen may be prepared upon sequential treatment of compounds of formula

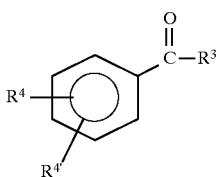

(X)

with aqueous basic ammonium cyanide followed by acid hydrolysis as described by L. B. Crast et al., U.S. Pat. No. 3,517,023 to produce compounds of formula

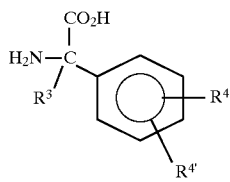

(XI)

which are then converted to the compounds of formula II, where $R^3$ is hydrogen by using standard protocols for derivatization of amino acids.

Compounds of formula II where $R^3$ is alkyl may be prepared upon sequential treatment of compounds of formula X with aqueous sodium cyanide and ammonium carbonate followed by heating with aqueous sodium or barium hydroxide as described by C. Bernhart et al., U.S. Pat. No. 5,268,375 to produce compounds of formula XI.

All compounds of formula XI may be converted to compounds of formula II where $R^3$ is alkyl using standard protocols for derivatization of amino acids; or converted to the compounds of formula V by heating in an alcohol such as ethanol containing a mineral acid such as HCl.

Compounds of formula II or V where $R^3$ is alkyl can be prepared in high optical purity upon treatment of compounds of formula XI with a reagent such as acetic anhydride in a solvent such as water to produce compounds of formula

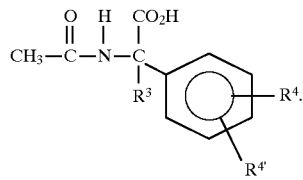

(XII)

Subsequent resolution of XII in a solvent such as ethanol employing a optically active amine such as α-methylbenzylamine and subsequent hydrolysis in a solvent such as water containing a strong mineral acid such as HCl generates optically active compounds of formula XI.

Compounds of formula VIII can be obtained by treatment of a p-hydroxyphenyl alkyl ketone or a p-halophenyl alkyl ketone, with a nitrating agent such as fuming nitric acid at a temperature of about −20° C. to 20° C. preferably at about −20° C. or 0° C. depending on whether $R^{2'''}$ is hydroxyl or halogen to generate a compound of formula

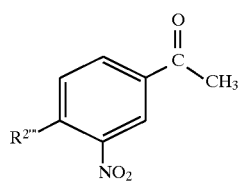

(XIII)

followed by, in the case of hydroxyl, optional alkylation with benzyl chloride in a solvent such as dimethylformamide or acetone in the presence of a base such as potassium carbonate to generate compounds of formula

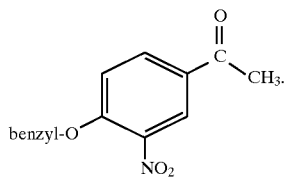

(XIV)

Subsequent reduction of the compounds of formula XIII or XIV in a solvent such as methanol using hydrogen in the presence of a catalyst such as platinum oxide or alternatively with stannous chloride in a solvent such as ethyl acetate followed by condensation of the reaction product or of a commercially available 3-aminophenyl alkyl ketone with a sulfonyl chloride in a solvent such as pyridine, generates compounds of the formula

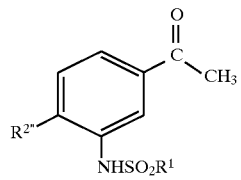

(XV)

where $R^{2''}$ is hydrogen, hydroxyl, halogen, or O-benzyl.

Compounds of formula XV where $R^{2''}$ is —$CO_2R^7$ can be prepared from compounds of formula XV where $R^{2''}$ is bromine by heating with a $Pd^{+2}$ catalyst and carbon monoxide in a solvent such as toluene/aqueous NaOH as described by V. Grushin, H. Alper, *Organometallics*, 12, 1890–1901 (1993) to generate the corresponding carboxylic acid which in turn can be transformed to compounds of formula XV where $R^{2''}$ is —$CO_2R^7$ by employing procedures known to those having ordinary skill in the art. Compounds of formula XV where $R^{2''}$ is —$CO_2R^7$ can be directly prepared from compounds of formula XV where $R^{2''}$ is bromine by the method of A. Schoenberg, I. Bartoletti, and R. F. Heck, *J. Org. Chem.*, 39, 3318–3326 (1974).

Alternatively, compounds of formula XV where $R^{2''}$ is —$CO_2R^7$ may be prepared from compounds of formula XV where $R^{2''}$ is O-benzyl by 1) sequential hydrogenolysis over a catalyst such as Pd in a solvent such as methanol; 2) conversion to the triflate upon reaction with trifluoromethanesulfonic anhydride in a solvent such as dichloromethane in the presence of a base such as pyridine; and 3) heating with $Pd(OAc)_2$ and 1,2-bis(diphenyl) phosphinoethane under an atmosphere of carbon monoxide in an alcohol solvent containing a base such as triethyl amine as described by U. Gerlach, T. Wollmann, *Tetrahedron Letters*, 33, 5499–5502 (1992).

Heating of compounds of formula XV in a solvent such as ethyl acetate containing cupric bromide, or with bromine in solvents such as methanol or tetrahydrofuran or methylene chloride generates all compounds of formula VIII where L' is bromine. Compounds of formula VIII may also be prepared according to A. A. Larsen et al., *J. Med. Chem.*, 10, 462 (1967) or U.S. Pat. No. 3,574,741.

Compounds of formula X are commercially available.

Compounds of formula III where L is bromide or iodide are prepared in high enantiomeric purity from compounds of formula VIII where $R^{2''}$ is hydrogen, halogen, —$CO_2R^7$ or O-benzyl and L' is Br by treatment with borane using a solvent such as tetrahydrofuran with a chiral auxiliary agent such as the compound

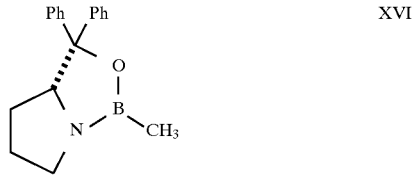

XVI (prepared as reported by E. J. Corey et al., *J. Org. Chem.*, 56, 442 (1991)) to generate compounds of formula

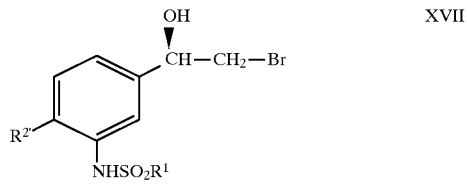

XVII

Subsequent treatment of compounds of formula XVII with an iodide source such as sodium iodide in a solvent such as hot acetone followed by reaction with a silylating agent such as triethylsilyl or t-butyldimethylsilyl chloride in a solvent such as pyridine generates the compounds of formula III where L is iodide.

The references cited above are incorporated by reference herein.

Preferred compounds of formula I are those where $R^1$ is lower alkyl, $R^2$ is hydroxyl, $R^3$ is lower alkyl and $R^4$ is alkoxy.

Most preferred compounds of formula I are those where one of $R^5$, $R^{5'}$ and $R^{5''}$ is —$(CH_2)_mPO(OR^6)OR^{6'}$; or the compounds of formula I where one of $R^5$, $R^{5'}$ and $R^{5''}$ is —$(CH_2)_mPO(OR^6)OR^{6'}$, m is the integer 1 and the others are hydrogen; or the compounds of formula I where $R^1$ is lower alkyl, $R^2$ is hydroxyl, $R^3$ is lower alkyl, $R^4$ is alkoxy and one of $R^5$, $R^{5'}$ and $R^{5''}$ is —$(CH_2)_mPO(OR^6)OR^{6'}$; or the compounds of formula I where $R^1$ is lower alkyl, $R^2$ is hydroxyl, $R^3$ is lower alkyl, $R^4$ is alkoxy and $R^5$, $R^{5'}$ and $R^{5''}$ are independently alkoxy; or the compounds of formula I where $R^1$ is unsubstituted lower alkyl, $R^2$ is hydroxyl, $R^3$ is unsubstituted lower alkyl, $R^4$ is lower alkoxy and one of $R^5$, $R^{5'}$ and $R^{5''}$ is —$(CH_2)_mPO(OR^6)OR^{6'}$.

The present compounds of formula I have activity at the beta 3 adrenergic receptor and are therefore useful, for example, in the treatment of diabetes, obesity, gastrointestinal diseases (such as inflammatory bowel disease, irritable bowel syndrome, nonspecific diarrhea, and peptic ulcer) and achalasia.

Thus a composition containing one (or a combination) of the compounds of this invention, may be administered to a species of mammal (e.g., humans) suffering from diabetes, obesity, an intestinal hypermotility disorder or achalasia as treatment therefor.

A single dose, or two to four divided daily doses, provided on a basis of about 0.1 to 100 mg per kilogram of body weight per day, preferably about 1 to 15 mg per kilogram of body weight per day is appropriate. The substance is preferably administered orally, but intranasal, transdermal and parenteral routes such as the subcutaneous, intramuscular, intravenous or intraperitoneal routes can also be employed.

The compounds of this invention can be formulated in combination with $beta_1$/$beta_2$ adrenergic blockers such as propranolol and nadolol or stimulants such as salbutamol. The compounds of formula I can also be formulated in combination with centrally (CNS) or systemically active agents that reduce food intake, such as leptin.

The compounds of formula I can be formulated for use in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Based on the literature, it is expected that these compounds may be useful for other indications such as treatment of depression and stress, regulation of intraocular pressure, treatment of conditions associated with increased protein breakdown such as during convalescence after surgery, treatment of triglyceridemia, hypercholesterolemia, atherosclerotic and cardiovascular diseases, and increasing high density lipoprotein levels. In addition, it is expected that these compounds may be useful as feed additives for fattening or improving weight gain or increasing lean body mass in animals and may therefore be used to decrease birth mortality and increase post-natal survival rates in animals.

In addition, based on the literature, compounds of formula I are expected to be useful for improving healing and preventing stomach ulcers (K. Kuratani et. al., *J. Pharmacol. Exp. Ther.*, 270, 559 (1994)). The compounds of formula I are also expected to be useful for regulating core temperature.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

(R), (S)-[[4-[[2-[[2-Hydroxy-2-[4-hydroxy-3-[(methylsulfonyl)amino]phenyl]ethyl]amino]-2-(4-methoxyphenyl)-1-oxopropyl]amino]phenyl]methyl] phosphonic acid, diethyl ester, trifluoroacetate

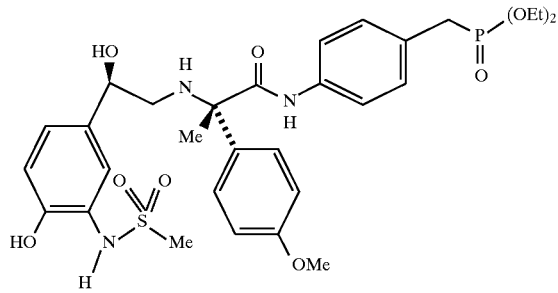

A. 5-Methyl-5-(4-methoxyphenyl)hydantoin

To a mechanically stirred 1:1 mixture of EtOH/H$_2$O (3 L) at 72° C. was added sequentially (NH$_4$)$_2$CO$_3$ (1.45 kg, 15.1 mol), NaCN (248 g, 5.1 mol), and 4-methoxyacetophenone (323 g, 2.15 mol). The stirred mixture was heated at 72° C. with monitoring by HPLC. After 67 hours, additional (NH$_4$)$_2$CO$_3$ (180 g, 1.88 mol) and NaCN (30 g, 0.61 mol) were added. After 70 hours, another portion of (NH$_4$)$_2$CO$_3$ (240 g, 2.5 mol) and NaCN (36 g, 0.73 mol) were added. After a total of 92 hours, the reaction mixture was cooled to 10° C. and filtered. The filter cake was washed with 6 L of H$_2$O prior to air drying to yield 461 g of pure title compound.

B. (S)-α-Amino-4-methoxy-α-methylbenzeneacetic acid, ethyl ester

To a suspension of 5-methyl-5-(4-methoxyphenyl) hydantoin (90 g, 0.408 mol) in 360 mL of water was added solid NaOH (90 g, 2.246 mol) and the final solution was heated to reflux for 30 hours. After cooling to room temperature, 720 mL of water was added; the solution was cooled to 10° C. and the pH was adjusted to 9 with 2N HCl. Acetic anhydride (1.28 mol, 121 mL) was added dropwise as the pH was kept at 9 by simultaneous addition of 2N NaOH (1410 mL). After stirring the final solution for 1 hour at room temperature, a small amount of insoluble material was removed by filtration through a Celite® pad which was then washed with water. The pH of the filtrate was adjusted to 1 with 12N HCl. After stirring for 15 minutes at 10° C., the precipitated material was filtered, washed with water (3×250 mL), and dried in vacuo at 40° C. to yield racemic α-acetamido-4-methoxy-α-methylbenzeneacetic acid (92.34 g, 95%, mp: 222° C.). A suspension of racemic α-acetamido-4-methoxy-α-methylbenzeneacetic acid (90.3 g. 381 mmol) in 4515 mL of EtOH (50 v/w) was heated to 40° C. (internal). To this suspension was added 49.12 mL (381 mmol) of (L)-(−)-α-methylbenzylamine. The warm solution was seeded with a few crystals of (S)-(+)-α-acetamido-4-methoxy-α-methylbenzeneacetic acid and stirred at room temperature (24° C.) for 24 hours. The desired diastereomeric salt was collected by filtration, washed with EtOH (2×75 mL) and several times with Et$_2$O and dried in vacuo at 40° C. to yield 38.95 g (57% optical yield). α$_D$: +67.8° (MeOH, c=1).

The above salt (78.42 g, 219 mmol) was suspended in 1427 mL of water and the pH adjusted to 1 with 2N HCl. After stirring for 30 minutes at room temperature, the precipitated (S)-(+)-α-acetamido-4-methoxy-α-methylbenzeneacetic acid was collected by filtration, washed with water (2×164 mL) and dried in vacuo at 40° C. in the presence of P$_2$O$_5$ to yield 51.44 g (101%, mp: 239°–240° C.) α$_D$: +86.5° (Phosphate buffer pH=7 c=1).

A suspension of (S)-(+)-α-acetamido-4-methoxy-α-methylbenzeneacetic acid (30 g, 126 mmol) in 4N HCl (300 mL) was refluxed for 2 hours and evaporated in vacuo to dryness. The residue was repeatedly dissolved in EtOH and evaporated again to dryness (4 liters of EtOH were used). The final solid was washed with tert-butyl methyl ether (4×100 mL) and finally with acetone (2×125 mL), dried in vacuo at 40° C. in presence of P$_2$O$_5$ to yield 26.92 g of (S)-α-amino-4-methoxy-α-methylbenzeneacetic acid, hydrochloride salt (92%, mp: >260° C.). α$_D$: 70.4° (1N HCl, c=1).

HCl gas was bubbled through a solution of (S)-α-amino-4-methoxy-α-methyl-benzeneacetic acid, hydrochloride salt (2.0 g, 8.6 mmol) in EtOH (25 mL) at 4° C. The solution was stirred for 1 hour at 20° C. before being refluxed for 5 hours. After cooling, the solution was concentrated in vacuo. The resulting oil was dissolved in CH$_2$Cl$_2$, and washed with aq. NaHCO$_3$; the aqueous phase was back-extracted with CH$_2$Cl$_2$. The combined organic fractions were washed with H$_2$O, brine and dried over Na$_2$SO$_4$ prior to concentration to yield the title compound as a yellow oil (1.75 g, 91%).

C. (R)-N-[5-[2-Iodo-1-[((1,1-dimethylethyl) dimethylsilyl)oxy]ethyl]-2-(phenylmethoxy)phenyl] methanesulfonamide

1. 1-[4-Hydroxy-3-nitrophenyl]ethanone

To mechanically stirred conc. H$_2$SO$_4$ (700 mL) at 3° C. was added p-hydroxyacetophenone (66.0 g, 480 mmol) followed by KNO$_3$ (48.3 g, 477 mmol) in two approximately equal portions about four minutes apart. An additional 3.76 g of KNO$_3$ was added after 1.67 hours to insure reaction completion. The reaction was slowly poured into 8 L crushed ice/water and extracted with 4 L ethyl acetate (EtOAc). The extract was concentrated in vacuo to a volume of ~1.25 L, 500 mL heptane were added and concentration was continued. Once a thick yellow suspension formed at 50° C., it was cooled to ~10° C. and filtered. The collected solids were washed with ~150 mL heptane and dried in vacuo at ~40° C. to give 81.8 g of the title compound.

2. 1-[4-Phenylmethoxy-3-nitrophenyl]ethanone

To a mechanically stirred DMF (260 mL) suspension of 1-[4-hydroxy-3-nitrophenyl]ethanone (51 g, 282 mmol) and K$_2$CO$_3$ (17 g, 847 mmol) was added benzyl bromide (68 mL, 572 mmol) followed by NaI (47 g, 313 mmol). After stirring overnight at 20° C., an additional 10 mL of benzyl bromide was added and the reaction was stirred for 15 more minutes. The reaction was quenched by the addition of 1.6 L water. The resulting suspension was stirred overnight and then filtered. The collected solids were washed 3×250 mL=750 mL water and dried in vacuo at ~55° C. to give 75 g crude product which was slurried in 1.3 L toluene at ~75° C., filtered hot through a 5.0 μm membrane, concentrated in vacuo to a volume of ~300 mL, diluted with 250 mL heptane, and the suspension cooled from ~60° C. to ambient. After filtration, the collected solids were washed with heptane and dried in vacuo at ~55° C. to give 64 g (84%) of the title compound.

3. 1-[4-Phenylmethoxy-3-aminophenyl]ethanone

A mechanically stirred MeOH (3.8 L) suspension containing 1-[4-phenylmethoxy-3-nitrophenyl]ethanone (76.5 g, 282 mmol) was degassed with argon for 40 minutes at ~10° C. prior to addition of PtO₂ (2.34 g, 10 mmol). Hydrogen was sparged into the reaction mixture at 8° C. to 10° C. via a subsurface gas inlet. After 8 hours, the completed reaction was degassed with Ar while being warmed to ~15° C., diluted with CHCl₃ (250 mL) and filtered. The filtrate was stripped to give 70 g crude product which, after trituration for ten minutes with i-PrOH (450 mL) at 60° C., yielded 57.4 (84%) of the title compound.

4. 1-[4-Phenylmethoxy-3-[(methylsulfonyl)amino]phenyl]ethanone

To a mechanically stirred 16° C. pyridine (270 mL) solution of 1-[4-phenylmethoxy-3-aminophenyl]ethanone (57.4 g, 238 mmol) under N₂, was added methanesulfonyl chloride (18.6 mL, 240 mmol). After 39 minutes, the completed reaction was quenched with 1.8 L H₂O and the resulting suspension stirred for ~2 hours before filtration. The collected solids were washed with H₂O (2×250 mL=500 mL) and partially air dried. These solids were dissolved in CHCl₃ (450 mL), the aqueous phase removed and heptane (475 mL) added with stirring. The resulting fine suspension was filtered after ~15 minutes, washed with hexane and dried in vacuo at 55° C. to give 59 g (78%) of the title compound.

5. 2-Bromo-1-[4-phenylmethoxy-3-[(methylsulfonyl)amino]phenyl]ethanone

To a mechanically stirred refluxing EtOAc (500 mL) suspension of CuBr₂ (41.5 g, 186 mmol) equipped with an Ar sparge was added a ~62° C. CHCl₃ (500 mL) solution of 1-[4-phenylmethoxy-3-[(methylsulfonyl)amino]phenyl]ethanone (25.5 g, 80 mmol). After 5.5 hours of reflux, HPLC showed 11.2 rel. area % unreacted starting material, 78.9 rel. area % of desired product and 9.8 rel. area % of dibrominated product. After cooling to 62° C. and dilution with 500 mL CHCl₃, the suspension was filtered hot and the filtrate concentrated to a volume of ~850 mL prior to addition of 250 mL heptane. The flocculent suspension was cooled to ~10° C. and filtered, washed with heptane and air-dried overnight to give 23.1 g (73%) of the title compound in 73% purity.

6. (R)-2-Bromo-1-[4-phenylmethoxy-3-[(methylsulfonyl)amino]phenyl]ethanol

A 25 mL round bottom flask with magnetic stirbar and toluene-filled Dean-Stark trap with reflux condenser and gas bubbler, was charged with (R)-α,α-diphenyl-2-pyrrolidinemethanol (1.13 g, 4.46 mmol) and trimethylboroxine (418 μL, 2.99 mmol) in toluene (11 mL) under N₂. The mixture was stirred at ambient temperature for ~30 minutes and then heated to reflux for 2.75 hours. Upon cooling, this solution was added to a stirred ~-13° C. THF (185 mL) solution under N₂ containing 2-bromo-1-[4-phenylmethoxy-3-[(methylsulfonyl)amino]phenyl]ethanone (14.25 g, 36 mmol). To this was added 5.2 mL of 10.1M BH₃.Me₂S (52 mmol) over ~5 minutes, keeping T≦-11.6° C. Upon completion of the reaction, HBr was bubbled through the solution until the pH was ~1 whereupon a solution of 50 mL MeOH in 100 mL methyl tert-butyl ether was carefully added. The mixture was washed with H₂O (4×100 mL=400 mL) (until the final wash had pH~4–5), diluted with EtOAc (50 mL), dried over Na₂SO₄. After solvent removal in vacuo, 12.84 g (90%) of crude title compound was obtained in 86% purity with an ee of 96.9%.

7. (R)-2-Iodo-1-[4-phenylmethoxy-3-[(methylsulfonyl)amino]phenyl]ethanol

A mixture of (R)-2-bromo-1-[4-phenylmethoxy-3-[(methylsulfonyl)amino]phenyl]ethanol (12.4 g, 31 mmol) and NaI (52 g, 346 mmol) were refluxed in acetone (190 mL) for 1.75 hours. After filtration, the filtrate was concentrated to a pasty red-brown solid which was partitioned between CH₂Cl₂ (150 mL) and H₂O (190 mL). The organic phase was washed with 150 mL ~23.5% w/w aq. sodium bisulfite and with H₂O (150 mL), dried over Na₂SO₄ and concentrated to give the title compound (12.72 g, 91%).

8. (R)-N-[5-[2-Iodo-1-[((1,1-dimethylethyl)dimethylsilyl)oxy]ethyl]-2-(phenylmethoxy)phenyl]methanesulfonamide To a stirred DMF (65 mL) solution containing (R)-2-iodo-1-[4-phenylmethoxy-3-[(methylsulfonyl)amino]phenyl]ethanol (12.7 g, 28 mmol), imidazole (5.25 g, 77 mmol), and 4-dimethylaminopyridine (0.30 g, 2.46 mmol) was added t-butyldimethylsilyl chloride (5.0 mL, 29.8 mmol). After 15 hours, the completed reaction was diluted with EtOAc (200 mL) and heptane (70 mL). The organic phase was washed 1×100 mL H₂O, 2×100 mL aq. sat. CuSO₄, 1×100 mL H₂O, 1×100 mL sat'd brine, and dried over Na₂SO₄. The filtrate was concentrated in vacuo to give 15.81 g of a tan solid which was dissolved in ~125 mL CH₂Cl₂ and diluted with 650 mL heptane. The mixture was concentrated in vacuo at 40° C. to 42° C. until solids were seen (~105 mL distillate were collected), cooled to ~15° C. and filtered. The collected solids were washed with heptane and dried in vacuo at 45° C. to give 11.1 g (70%) of the title compound.

Mass (M+NH₄) 579; (M—H) 560. HPLC: >99% pure, Shimadzu, YMC S3 ODS (6.0×150 mm); flow rate of 1.5 mL/minute; detection at 217 nM; gradient elution 0–100% B over 30 minutes (A=10% MeOH, 90% H₂O, 0.2% H₃PO₄ and B=90% MeOH, 10% H₂O, 0.2% H₃PO₄); retention time=35 minutes.

D. (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic Acid A mixture of (S)-α-amino-4-methoxy-α-methylbenzeneacetic acid, ethyl ester (5.08 g, 22.8 mmol), the title C compound (12.8 g, 22.8 mmol) and N,N-diisopropylethylamine (19 mL, 109 mmol) in THF (35 mL) was heated at 140° C. in a sealed flask for 120 hours. The reaction mixture was cooled, diluted with EtOAc and washed with brine (3 ×). The organic layer was dried over anhydrous Na₂SO₄ and concentrated to obtain an oil which was purified by SiO₂ column eluting with 15 to 25% EtOAc/hexanes to obtain 8.8 g (98% purity, 13.2 mmol, 58%) of (R), (S)-α-[[2-[((1,1-dimethylethyl)dimethylsilyl)oxy]-2-[4-phenylmethoxy-3-[(methylsulfonyl)amino]phenyl]ethyl]amino]-4-methoxybenzeneacetic acid, ethyl ester.

To a stirred 0° C. solution of (R), (S)-α-[[2-[((1,1-dimethylethyl)dimethylsilyl)oxy]-2-[4-phenylmethoxy-3-[(methylsulfonyl)amino]phenyl]ethyl]amino]-4-methoxybenzeneacetic acid, ethyl ester (8.8 g, 98% purity, 13.2 mmol) in THF (44 mL) under Ar was added MeOH (44 mL) and H₂O (22 mL) followed by LiOH monohydrate (3.01 g, 71.7 mmol). The resulting solution was stirred 40 hours at 20° C. whereupon it was concentrated in vacuo and diluted with EtOAc and H₂O. After adding brine and adjusting the pH to 3 with 1N HCl, the mixture was extracted 3 × with EtOAc. The EtOAc extracts were diluted 1:1 with CH₂Cl₂, washed with brine, dried over Na₂SO₄ to yield after concentration 8.16 g of (R), (S)-α-[[2-((1,1-dimethylethyl)dimethylsilyl)oxy]-2-[4-phenylmethoxy-3-[(methylsulfonyl)amino]phenyl]ethyl]amino]-4-methoxybenzeneacetic acid as a solid foam.

A solution of (R), (S)-α-[[2-[((1,1-dimethylethyl)dimethylsilyl)oxy]-2-[4-phenylmethoxy-3-[

(methylsulfonyl)amino]phenyl]ethyl]amino]-4-methoxybenzeneacetic acid (4.04 g, 6.5 mmol) in MeOH (50 mL) containing 0.42 g of 10% Pd/C was sparged with $H_2$ at 20° C. By TLC (10% MeOH/$CH_2Cl_2$), the reaction was complete after 40 minutes whereupon the reaction mixture was filtered and concentrated in vacuo to obtain 3.8 g of the title compound as a solid foam.

E. (R), (S)-[[4-[[2-[[2-Hydroxy-2-[4-hydroxy-3-[(methylsulfonyl)amino]phenyl]ethyl]amino]-2-(4-methoxyphenyl)-1-oxopropyl]amino]phenyl]methyl] phosphonic Acid, Diethyl Ester, Trifluoroacetate A solution of 1,2-dichloroethane (2.3 mL) and DMF (0.93 mL) containing (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid (500 mg, 0.93 mmol) was cooled to 0° C. and 1-(3-dimethylaminopropyl)-3-ethylcarbodiimide HCl (EDCI) (212 mg, 1.11 mmol) and 1-hydroxy-7-azabenztriazole (HOAT) (151 mg, 1.11 mmol) was added. After stirring 10 minutes, diethyl 4-aminobenzylphosphonate (270 mg, 1.11 mmol) was added; the dark solution stirred overnight at 20° C. whereupon the reaction was quenched with aq. $NaHCO_3$ and extracted 4 × with EtOAc. The EtOAc extracts after washing with aq. $NaHCO_3$ and brine prior to drying over $Na_2SO_4$ were concentrated in vacuo. The resulting oil was chromatographed on silica gel; (R), (S)-[[4-[[2-[[2-[((1,1-dimethylethyl)dimethylsilyl)oxy]-2-[4-hydroxy-3-[(methylsulfonyl)amino]phenyl]ethyl]amino]-2-(4-methoxyphenyl)-1-oxopropyl]amino]phenyl]methyl] phosphonic acid, diethyl ester (415 mg, 58%) was eluted with 1:3 to 1:8 hexane/EtOAc.

A mixture of (R), (S)-[[4-[[2-[[2-[((1,1-dimethylethyl)dimethylsilyl)oxy]-2-[4-hydroxy-3-[(methylsulfonyl)amino]phenyl]ethyl]amino]-2-(4-methoxyphenyl)-1-oxopropyl]amino]phenyl]methyl]phosphonic acid, diethyl ester (360 mg, 0.47 mmol) and ammonium fluoride (900 mg, 24 mmol) in HOAc (3.6 mL) and MeOH (3.6 mL) were stirred 5 hours at 45° C. Silica gel chromatography eluting with 1 to 7% MeOH/$CH_2Cl_2$ yielded 276 mg of the title compound as the free base which was converted to the TFA salt upon sequential dissolution in 2.1 mL MeOH, addition of 80 μL of TFA followed by 100 mL of $H_2O$ and lyophilization.

$^1$H NMR (300 MHz, $CD_3OD$), δ 1.25 (t, 6H), 2.18 (s, 3H), 2.62–2.84 (m, 2H), 2.90 (s, 3H), 3.21 (d, 2H), 3.83 (s, 3H), 3.98–4.09 (m, 4H), 4.76 (dd, 1H), 6.85 (d, 1H), 7.00 (dd, 1H), 7.06 (d, 2H), 7.25–7.29 (m, 3H), 7.49–7.55 (m, 4H). $^{13}$C NMR (100 MHz, $CDCl_3$). δ 16.3 (d), 22.0, 32.7 (d), 39.0, 50.8, 55.3, 62.7 (d), 64.4, 72.7, 114.0, 116.3, 120.2 (d), 121.4, 123.9, 124.3, 125.8 (d), 126.9, 129.8 (d), 134.7, 135.2, 136.9 (d), 148.3, 158.9, 173.1. Mass (M+H)=650. HPLC: 100% pure, Shimadzu, YMC S3 ODS (6.0×150 mm); flow rate of 1.5 mL/minute; detection at 217 nM; gradient elution 0–100% B over 30 minutes (A=10% MeOH, 90% $H_2O$, 0.2% $H_3PO_4$ and B=90% MeOH, 10% $H_2O$, 0.2% $H_3PO_4$); retention time=19.9 minutes.

EXAMPLE 2

(R), (S)-α-[[2-Hydroxy-2-[4-hydroxy-3-[(methylsulfonyl)amino]phenyl]ethyl]amino]-4-methoxy-α-methyl-N-(3-phenoxyphenyl) benzeneacetamide, Trifluoroacetate

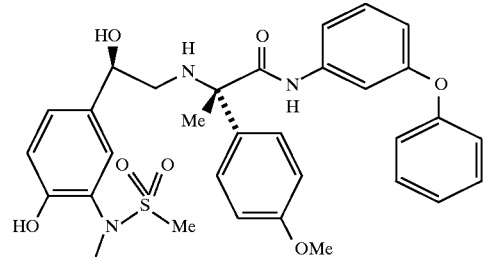

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with commercial 3-phenoxyaniline to generate the title compound.

$^1$H NMR (270 MHz, $CD_3OD$), δ 2.12 (s, 3H), 2.59 (dd, 1H), 2.78 (t, 1H), 2.89 (s, 3H), 3.82 (s, 3H), 4.72 (dd, 1H), 6.75 (m, 1H), 6.82 (d, 1H), 6.93–7.15 (m, 6H), 7.22–7.40 (m, 6H), 7.49 (d, 2H). Mass (M+H)=592. HPLC: >93% pure, retention time 24.3 minutes; protocol described in Example 1.

EXAMPLE 3

(R), (S)-α-[[2-Hydroxy-2-[4-hydroxy-3-[(methylsulfonyl)amino]phenyl]ethyl]amino]-4-methoxy-α-methyl-N-[4-(2-oxazolyl)phenyl] benzeneacetamide, Trifluoroacetate

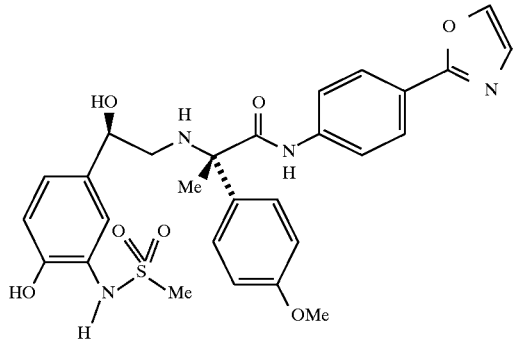

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with 4-(2-oxazolyl)aniline to generate the title compound. The 4-(2-oxazolyl)aniline was prepared by treating 4-nitrobenzoyl chloride sequentially with 1,2,3-triazole at 140° C. in sulfolane containing $K_2CO_3$ to generate 4-(2-oxazolyl) nitrobenzene which was reduced to the desired aniline with $Na_2S_2O_4$ in THF/$H_2O$ at 90° C.

$^1$H NMR (400 MHz, $CD_3OD$), δ 2.20 (s, 3H), 2.61–2.88 (m, 2H), 2.90 (s, 3H), 3.83 (s, 3H), 4.75 (m, 1H), 6.85 (d, 1H), 7.01 (d, 1H), 7.07 (d, 2H), 7.27 (m, 2H), 7.54 (d, 2H), 7.74 (d, 2H), 7.97 (m, 3H). Mass (M+H)=567. HPLC: 98.9% pure, retention time 18.9 minutes; protocol described in Example 1.

EXAMPLE 4

(R), (S)-α-[[2-Hydroxy-2-[4-hydroxy-3-[(methylsulfonyl)amino]phenyl]ethyl]amino]-4-methoxy-α-methyl-N-[3-(2-oxazolyl)phenyl]benzeneacetamide, Trifluoroacetate

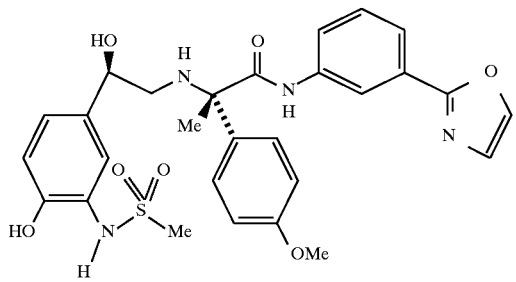

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with 3-(2-oxazolyl)aniline to generate the title compound. The 3-(2-oxazolyl)aniline was prepared by treating 3-nitrobenzoyl chloride sequentially with 1,2,3-triazole at 140° C. in sulfolane containing $K_2CO_3$ to generate 3-(2-oxazolyl)nitrobenzene which was reduced to the desired aniline with $Na_2S_2O_4$ in THF/$H_2O$ at 90° C.

$^1$H NMR (400 MHz, CD$_3$OD), δ 2.21 (s, 3H), 2.65–2.85 (m, 2H), 2.91 (s, 3H), 3.83 (s, 3H), 4.83 (m, 1H), 6.85 (d, 1H), 7.01 (d, 1H), 7.07 (d, 2H), 7.27 (s,1H), 7.31 (s,1H), 7.46 (t,1H), 7.55 (d, 2H), 7.67 (m, 1H), 7.80 (d, 1H), 8.00 (s, 1H), 8.30 (s, 1H). Mass (M+H)=567. HPLC: 96.8% pure, retention time 19.5 minutes; protocol described in Example 1.

EXAMPLE 5

(R), (S)-α-[[2-Hydroxy-2-[4-hydroxy-3-[(methylsulfonyl)amino]phenyl]ethyl]amino]-4-methoxy-α-methyl-N-[4-(2-thiazolyl)phenyl]benzeneacetamide, Trifluoroacetate

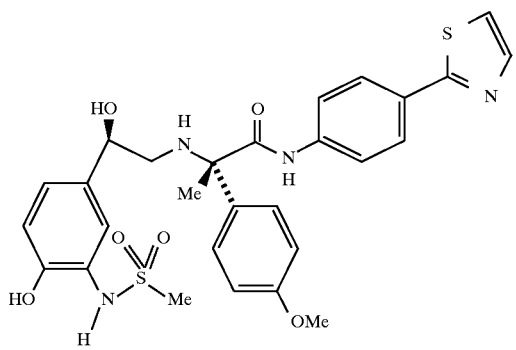

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with 4-(2-thiazolyl)aniline to generate the title compound. The preparation of 4-(2-thiazolyl)aniline entailed n-BuLi promoted metalation of thiazole at −75° C. to −60° C. followed by alkylation with Me$_3$SnCl. The resulting stannane was coupled with 4-nitrophenyl iodide under Ar in THF containing ($φ_3$P)$_2$PdCl$_2$. Subsequent reduction with Na$_2$S$_2$O$_4$ in THF/$H_2O$ at 100° C. for 20 hours completed the synthesis of 4-(2-thiazolyl)aniline.

$^1$H NMR (400 MHz, CD$_3$OD), δ 2.19 (s,3H), 2.65 (dd, 1H), 2.82 (dd, 1H), 2.90 (s, 3H), 3.83 (s, 3H), 4.76 (dd, 1H), 6.84 (d, 1H), 7.01 (dd, 1H), 7.07 (d, 2H), 7.26 (d, 1H), 7.54 (d, J 9.0 Hz, 2H), 7.63 (d, 2H), 7.67 (d, 2H), 8.13 (s,1H), 8.94 (s,1H). Mass (M+H)=583. HPLC: 100% pure, retention time 19.3 minutes; protocol described in Example 1.

EXAMPLE 6

(R), (S)-α-[[2-Hydroxy-2-[4-hydroxy-3-[(methylsulfonyl)amino]phenyl]ethyl]amino]-4-methoxy-α-methyl-N-[3-(2-thiazolyl)phenyl]benzeneacetamide, Trifluoroacetate

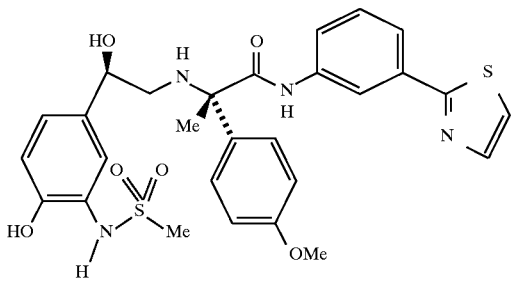

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with 3-(2-thiazolyl)aniline to generate the title compound. The preparation of 3-(2-thiazolyl)aniline entailed n-BuLi promoted metalation of thiazole at −75° C.—−60° C. followed by alkylation with Me$_3$SnCl. The resulting stannane was coupled with 3-nitrophenyl iodide under Ar in THF containing ($φ_3$P)$_2$PdCl$_2$. Subsequent reduction with Na$_2$S$_2$O$_4$ in THF/$H_2O$ at 100° C. for 20 hours completed the synthesis of 3-(2-thiazolyl)aniline.

$^1$H NMR (300 MHz, CD$_3$OD), δ 1.74 (s, 3H), 2.60 (dd, 1H), 2.81 (dd, 1H), 2.89 (s, 3H), 3.73 (s, 3H), 4.70 (dd, 1H), 6.84–6.90 (m, 3H), 7.08 (dd, 1H), 7.31–7.49 (m, 6H), 7.94 br s(1H), 8.10 (s, 1H), 8.88 (s, 1H). $^{13}$C NMR (76 MHz, CD$_3$OD) δ 22.4, 39.6, 52.4, 55.7, 65.8, 74.0, 114.8, 116.4, 119.4, 121.5, 123.6, 124.6, 125.6, 125.7, 128.6, 130.7, 132.6, 135.8, 136.1, 139.7, 140.2, 140.8, 150.8, 154.6, 160.4, 176.1. Mass (M+H)=583. HPLC: 100% pure, retention time 19.9 minutes; protocol described in Example 1.

EXAMPLE 7

(R), (S)-α-[[2-Hydroxy-2-[4-hydroxy-3-[(methylsulfonyl)amino]phenyl]ethyl]amino]-4-methoxy-α-methyl-N-[3-chloro-4-(2-thiazolyl)phenyl]benzeneacetamide, Trifluoroacetate

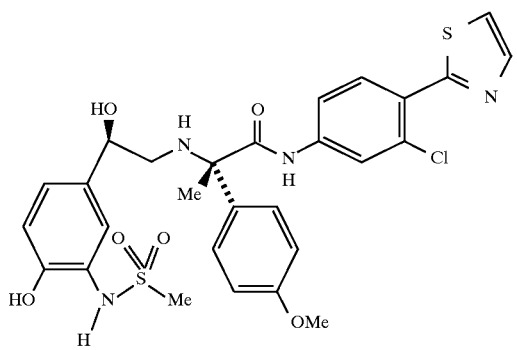

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with 3-chloro-4-(2-thiazolyl)aniline to generate the title compound. The preparation of 3-chloro-4-(2-thiazolyl)aniline entailed n-BuLi promoted metalation of thiazole at −75° C. to −60° C. followed by alkylation with Me$_3$SnCl. The resulting stannane was coupled with 3-chloro-4-nitrophenyl iodide under Ar in THF containing (φ$_3$P)$_2$PdCl$_2$. Subsequent reduction with Na$_2$S$_2$O$_4$ in THF/H$_2$O at 100° C. for 20 hours completed the synthesis of 3-chloro-4-(2-thiazolyl)aniline.

$^1$H NMR (300 MHz, CD$_3$OD), δ 1.72 (s, 3H), 2.57 (dd, 1H), 2.83 (dd, 1H), 2.91 (s, 3H), 3.76 (s, 3H), 4.70 (dd, 1H), 6.86–6.91 (m, 3H), 7.09 (dd, 1H), 7.41–7.53 (m, 5H), 7.80 d(1H), 8.04 (s, 1H), 9.01 (s, 1H). $^{13}$C NMR (76 MHz, CD$_3$OD) δ 22.5, 39.7, 52.4, 55.7, 65.8, 74.0, 114.8, 116.4, 119.9, 122.2, 124.8, 125.7 (2 signals), 128.5, 132.7, 133.6, 135.9, 136.1, 136.5, 141.0, 143.0, 150.9, 155.7, 160.5, 176.3. Mass (M+H)=617. HPLC: 100% pure, retention time 21.4 minutes; protocol described in Example 1.

EXAMPLE 8

(R), (S)-α-[[2-Hydroxy-2-[4-hydroxy-3-[(methylsulfonyl)amino]phenyl]ethyl]amino]-4-methoxy-α-methyl-N-[3-chloro-4-(2-oxazolyl)phenyl]benzeneacetamide, Trifluoroacetate

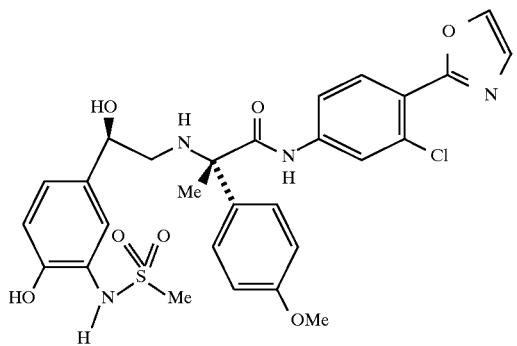

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with 3-chloro-4-(2-oxazolyl)aniline to generate the title compound. The 4-(2-oxazolyl)-3-chloroaniline was prepared by treating commercial 3-chloro-4-nitrobenzoyl chloride sequentially with 1,2,3-triazole at 140° C. in sulfolane containing K$_2$CO$_3$ to generate 3-chloro-4-(2-oxazolyl)nitrobenzene which was reduced to the desired aniline with Na$_2$S$_2$O$_4$ in THF/H$_2$O at 90° C.

$^1$H NMR (300 MHz, CD$_3$OD), δ 2.19 (s, 3H), 2.61–2.88 (m, 2H), 2.90 (s, 3H), 3.83 (s, 3H), 4.86 (m, 1H), 6.85 (d, 1H), 7.07 (dd,2H),7.25 (d,1H), 7.35 (s,1H), 7.54 (d,2H), 7.62 (d,1H), 7.87–8.05 (m,3H). Mass (M+H)=600. HPLC: 97.2% pure, retention time 20.76 minutes; protocol described in Example 1.

EXAMPLE 9

(R), (S)-α-[[2-Hydroxy-2-[4-hydroxy-3-[(methylsulfonyl)amino]phenyl]ethyl]amino]-4-methoxy-α-methyl-N-[3-(2-oxazolyl)-4-chlorophenyl]benzeneacetamide, Trifluoroacetate

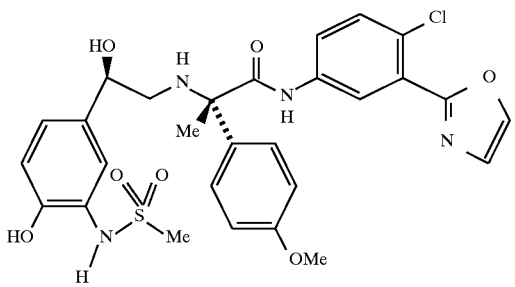

Following the procedure described in part E of Example 1 (R), (S)-α-[[[-((1,1-dimethylethyl)dimethylsilyl)oxy]-2-[4-hydroxy-3-[(methylsulfonyl)amino]phenyl]ethyl]amino]-4-methoxybenzeneacetic acid was condensed with 3-(2-oxazolyl)-4-chloroaniline to generate the title compound. The 3-(2-oxazolyl)-4-chloroaniline was prepared by treating commercial 4-chloro-3-nitrobenzoyl chloride sequentially with 1,2,3-triazole at 140° C. in sulfolane containing K$_2$CO$_3$ to generate 4-chloro-3-(2-oxazolyl)nitrobenzene which was reduced to the desired aniline with Na$_2$S$_2$O$_4$ in THF/H$_2$O at 90° C.

$^1$H NMR (270 MHz, CD$_3$OD), δ 1.74 (s, 3H), 2.60 (m, 1H), 2.85 (dd, 1H), 2.90 (s, 3H), 3.76 (s, 3H), 4.62 (t, 1H), 4.73 (m, 1H), 6.85 (d, 2H), 6.88 (s, 1H), 7.19 (s, 1H), 7.42 (m, 1H), 7.47 (d, 2H), 7.64 (m, 1H), 7.75 (s, 1H), 7.80 (m, 1H), 7.84 (s, 1H), 8.20 (m, 1H). $^{13}$C NMR (67 MHz, CD$_3$OD) δ 22.9, 40.0, 52.7, 56.0, 66.2, 74.3, 115.2, 116.7, 122.7, 123.8, 124.8, 125.9, 128.1, 128.5, 128.7, 128.9, 136.2, 137.1, 141.0, 141.6, 151.2, 160.8, 176.8. HPLC: 92% pure, retention time 18.3 minutes; protocol described in Example 1.

EXAMPLE 10

(R), (S)-α-[[2-Hydroxy-2-[4-hydroxy-3-[(methylsulfonyl)amino]phenyl]ethyl]amino]-4-methoxy-α-methyl-N-(3-acetylphenyl)benzeneacetamide, Trifluoroacetate

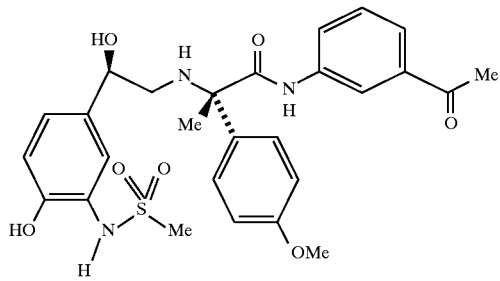

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with commercial 3-acetylaniline to generate the title compound.

$^1$H NMR (270 MHz, CD$_3$OD), δ 2.22 (s, 3H), 2.58 (s, 3H), 2.70–2.86 (m, 2H), 2.92 (s, 3H), 3.83 (s, 3H), 4.80 (dd, 1H), 6.85 (d, 1H), 7.01–7.11 (m, 3H), 7.28 (s, 1H), 7.43–7.60 (m, 3H), 7.72–7.85 (m, 2H), 8.19 (s, 1H). $^{13}$C NMR (67 MHz, CD$_3$OD) δ 19.31, 26.74, 39.67, 50.99, 56.00, 69.01, 69.99, 115.92, 116.70, 121.68, 124.19, 125.40, 126.03, 126.75, 130.29, 130.55, 133.69, 139.02, 139.48, 151.60, 162.69, 170.87, 199.98. Mass (M+H)=542. Calculated for 2.75 H$_2$O and 1.12 mol TFA:

|   | Calc. | Found |
|---|-------|-------|
| C | 48.85 | 48.39 |
| H | 5.28  | 4.91  |
| N | 5.85  | 6.37  |
| S | 4.46  | 4.60  |
| F | 8.88  | 8.78  |

HPLC: 99% pure, retention time 17.6 minutes; protocol described in Example 1.

EXAMPLE 11

(R), (S)-α-[[2-Hydroxy-2-[4-hydroxy-3-[(methylsulfonyl)amino]phenyl]ethyl]amino]-4-methoxy-α-methyl-N-(3-aminosulfonylphenyl)benzeneacetamide

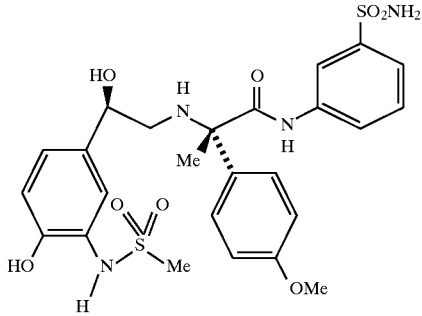

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with 3-aminosulfonylaniline to generate the title compound which was isolated as the free base. The 3-aminosulfonylaniline was prepared by Pd/C catalyzed reduction of commercial 3-nitrobenzenesulfonamide.

$^1$H NMR (270 MHz, CD$_3$OD), δ 1.72 (s, 3H), 2.59 (dd, 1H), 2.80 (dd, 1H), 2.89 (s, 3H), 3.77 (s, 3H), 4.68 (m, 1H), 6.88 (m, 3H), 7.08 (dd, 1H), 7.40–7.50 (m, 4H), 7.60 (m, 2H), 8.20 (m, 1H). Mass (M+H)=579. HPLC: 97.2% pure, retention time 14.4 minutes; protocol described in Example 1.

EXAMPLE 12

(R), (S)-α-[[2-Hydroxy-2-[4-hydroxy-3-[(methylsulfonyl)amino]phenyl]ethyl]amino]-4-methoxy-α-methyl-N-[(3-[[(propylamino)carbonyl]amino]phenyl)benzeneacetamide, Trifluoroacetate

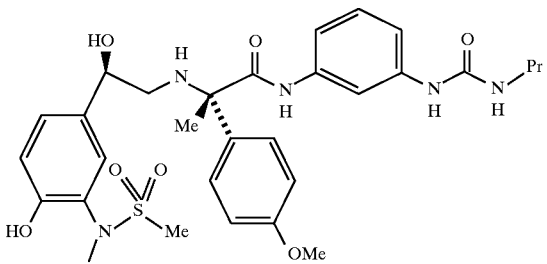

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with N-3-aminophenyl-N'-propylurea to generate the title compound. The N-3-aminophenyl-N'-propylurea was prepared by sequentially treating commercial 3-nitrophenylisocyanate with PrNH$_2$ in THF at 20° C. followed by reduction with Na$_2$S$_2$O$_4$ in THF/H$_2$O at 100° C.

$^1$H NMR (300 MHz, CD$_3$OD), δ 0.92 (t, 3H), 1.45–1.57 (m, 2H), 1.70 (s, 3H), 2.57 (dd, 1H), 2.75 (dd, 1H), 2.88 (s, 3H), 3.12 (t, 2H), 3.74 (s, 3H), 4.67 (dd, 1H), 6.86 (d, 2H), 6.87 (m, 1H), 6.97–7.18 (m, 4H), 7.38–7.43 (m, 3H), 7.50 (m, 1H). $^{13}$C NMR (76 MHz, CD$_3$OD) δ 11.7, 22.6, 24.3, 39.5, 42.6, 52.4, 55.7, 65.6, 74.0, 112.3, 114.7, 115.6, 116.2, 116.4, 124.7, 125.6, 125.7, 128.6, 130.0, 136.0, 136.1, 139.6, 141.4, 150.9, 158.2, 160.4, 175.9. Mass (M+H)=600. HPLC: 98.7% pure, retention time 18.7 minutes; protocol described in Example 1.

EXAMPLE 13

(R), (S)-α-[[2-Hydroxy-2-[4-hydroxy-3-[(methylsulfonyl)amino]phenyl]ethyl]amino]-4-methoxy-α-methyl-N-[(4-[[(propylamino)carbonyl]amino]phenyl)benzeneacetamide, Trifluoroacetate

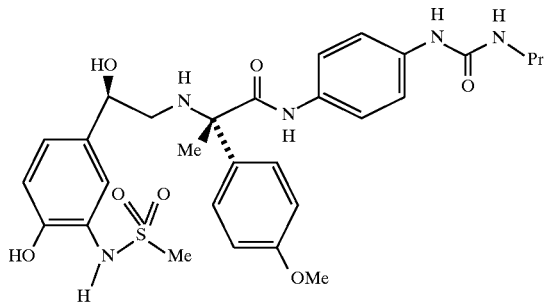

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with N-4-aminophenyl-N'-propylurea to generate the title compound. The N-4-aminophenyl-N'-propylurea was prepared by sequentially treating commercial 4-nitrophenyl isocyanate with PrNH$_2$ in THF at 20° C. followed by reduction with Na$_2$S$_2$O$_4$ in THF/H$_2$O at 100° C.

$^1$H NMR (400 MHz, CD$_3$OD), δ 0.94 (t, 3H), 1.51–1.56 (m, 2H), 2.16 (s, 3H), 2.64 (dd, 1H), 2.79 (t, 1H), 2.90 (s, 3H), 3.14 (t, 2H), 3.82 (s, 3H), 4.75 (dd, 1H), 6.84 (d, 1H), 6.98 (d, 1H), 7.05 (dd, 2H), 7.25 (d, 1H), 7.31 (d, 2H), 7.40 (d, 2H), 7.52 (d, 2H). Mass (M+H)=600. HPLC: 100% pure, retention time 18.0 minutes; protocol described in Example 1.

EXAMPLE 14

(R), (S)-[3-[[2-[[2-Hydroxy-2-[4-hydroxy-3-[(methylsulfonyl)amino]phenyl]ethyl]amino]-2-(4-methoxyphenyl)-1-oxopropyl]amino]phenyl)]carbamic Acid, Propyl Ester, Trifluoroacetate

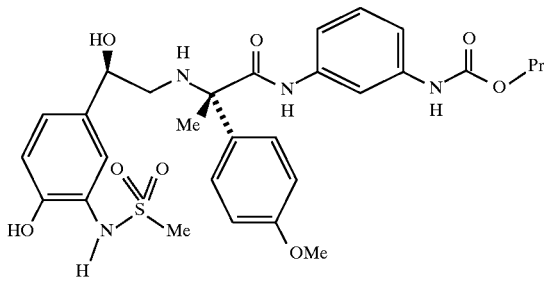

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]amino]-4-methoxybenzeneacetic acid was condensed with 3-aminophenylcarbamic acid, propyl ester to generate the title compound. The 3-aminophenylcarbamic acid, propyl ester was prepared by sequentially treating commercial 3-nitrophenyl isocyanate with PrOH containing Et$_3$N at 80° C. for 12 hours followed by reduction with Na$_2$S$_2$O$_4$ in THF/H$_2$O at 100° C.

$^1$H NMR (300 MHz, CD$_3$OD), δ 0.97 (t, 3H), 1.62–1.74 (m, 2H), 1.71 (s, 3H), 2.57 (dd, 1H), 2.76 (dd, 1H), 2.88 (s, 3H), 3.75 (s, 3H), 4.06 (t, 2H), 4.67 (dd, 1H), 6.84–6.89 (m, 3H), 7.02–7.09 (m, 2H), 7.14–7.19 (m, 2H), 7.39–7.43 (m, 3H), 7.63 (m, 1H). $^{13}$C NMR (76 MHz, CD$_3$OD) δ 10.7, 22.6, 23.4, 39.5, 52.4, 55.7, 65.6, 67.6, 74.0, 112.1, 114.7, 115.9, 116.2, 116.4, 124.6, 125.7, 128.6, 130.0, 136.0, 136.1, 139.7, 150.9, 156.1, 160.4, 175.9 (1 aromatic carbon unresolved). Mass (M+H)=601. HPLC: 99.0% pure, retention time 21.1 minutes; protocol described in Example 1.

EXAMPLE 15

(R), (S)-α-[[2-Hydroxy-2-[4-hydroxy-3-[(methylsulfonyl)amino]phenyl]ethyl]amino]-4-methoxy-α-methyl-N-(3-aminosulfonyl-4-chlorophenyl)benzeneacetamide

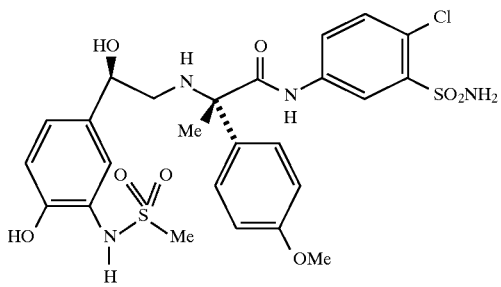

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]-amino]-4-methoxybenzeneacetic acid was condensed with 3-aminosulfonyl-4-chloroaniline to generate the title compound which was isolated as the free base. The 3-aminosulfonyl-4-chloroaniline was prepared by reduction of commercial 2-chloro-5-nitrobenzenesulfonamide with SnCl$_2$ in EtOAc.

$^1$H NMR (400 MHz, CD$_3$OD): δ 8.37 (d, 1H), 7.64 (dd, 1H), 7.48–7.42 (m, 4H), 7.37 (d, 1H), 7.06 (dd, 1H), 6.91–6.84 (m, 3H), 4.68 (dd, 1H), 3.77 (s, 3H), 2.90 (s, 3H), 2.76 (dd, 1H), 2.56 (dd, 1H), 1.73 (s, 3H). Mass Spec (ESI) (M+H)$^+$=613. HPLC: Purity 96%; retention time=15.14 minutes; protocol described in Example 1.

EXAMPLE 16

(R), (S)-[[4-[[2-[[2-Hydroxy-2-[4-hydroxy-3-[(methylsulfonyl)amino]phenyl]ethyl]amino]-2-(4-methoxyphenyl)-1-oxopropyl]amino]-3-chlorophenyl]methyl]phosphonic Acid, Diethyl Ester, Trifluoroacetate

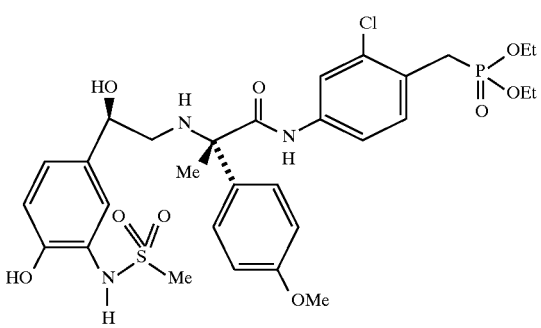

Following the procedure described in part E of Example 1 (R), (S)-α-[[2-[((1,1-dimethylethyl)dimethylsilyl)oxy]-2-

[4-hydroxy-3-[(methylsulfonyl)amino]phenyl]ethyl]-amino]-4-methoxybenzeneacetic acid was condensed with diethyl 3-chloro-4-aminobenzylphosphonate to generate the title compound. The diethyl 3-chloro-4-aminobenzylphosphonate was prepared from commercial 2-chloro-4-nitrobenzoic acid upon sequential treatment with 1) diborane in THF; 2) $\phi_3P,CBr_4$ in $CH_2Cl_2$; 3) $P(OEt)_3$ at 125° C.; and 4) reduction with $Na_2S_2O_4$ in $THF/H_2O$ at 100° C.

$^1$H NMR (300 MHz, $CD_3OD$), δ 1.27 (t, 6H), 2.17 (s, 3H), 2.64 (dd, 1H), 2.81 (dd, 1H), 2.90 (s, 3H), 3.40 (d, 2H), 3.82 (s, 3H), 4.00–4.12 (m, 4H), 4.77 (m, 1H), 6.85 (d, 1H), 6.97–7.09 (m, 3H), 7.26 (d, 1H), 7.35–7.45 (m, 2H), 7.49–7.54 (m, 2H), 7.83 (d, 1H). $^{13}$C NMR (100 MHz, $CD_3OD$) δ 16.6 (d), 19.2, 30.6 (d), 39.7, 51.0, 56.0, 63.9 (d), 69.0, 70.0, 115.9, 116.6, 120.4 (d), 122.6, 124.3, 125.4, 125.8, 126.1, 127.3 (d), 130.6, 133.1 (d), 133.8, 135.4 (d), 139.2 (d), 151.7, 162.7, 170.8. Mass (M+H)=684. HPLC: 96.3% pure, retention time 21.8 minutes; protocol described in Example 1.

EXAMPLE 17

(R), (S)-α-[[2-Hydroxy-2-[4-hydroxy-3-[(methylsulfonyl)amino]phenyl]ethyl]amino]-4-methoxy-α-methyl-N-[3-[2-(dimethylamino)ethoxy]phenyl]benzeneacetamide, Trifluoroacetate

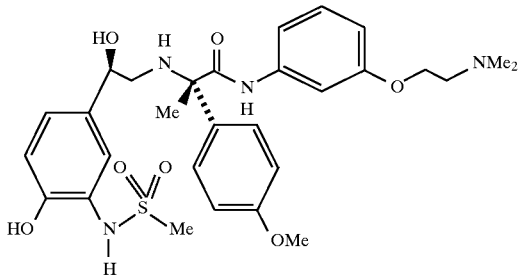

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]-amino]-4-methoxybenzeneacetic acid was condensed with 3-[2-(dimethylamino)ethoxy]aniline to generate the title compound. The 3-[2-(dimethylamino)ethoxy]aniline was prepared by treating commercial 3-aminophenol with diethyl azo dicarboxylate, $\phi_3P$, and 2-(dimethylamino)ethanol in THF.

$^1$H NMR (300 MHz, $CD_3OD$), δ 2.18 (s, 3H), 2.69–2.85 (m, 2H), 2.90 (s, 3H), 2.98 (s, 6H), 3.60 (m, 2H), 3.82 (s, 3H), 4.34 (m, 2H), 4.87 (m, 1H), 6.84 (m, 2H), 7.01–7.15 (m, 4H), 7.27 (m, 2H), 7.45 (s,1H). 7.52 (d, 2H). Mass (M+H)=587. HPLC: 96% pure, retention time 11.5 minutes; protocol described in Example 1.

EXAMPLE 18

(R), (S)-α-[[2-Hydroxy-2-[4-hydroxy-3-[(methylsulfonyl)amino]phenyl]ethyl]amino]-4-methoxy-α-methyl-N-[4-[2-(dimethylamino)ethoxy]phenyl]benzeneacetamide, Trifluoroacetate

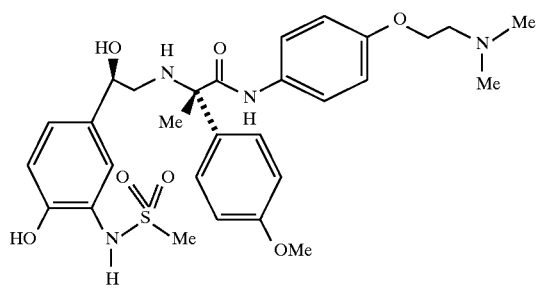

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]-amino]-4-methoxybenzeneacetic acid was condensed with 4-[2-(dimethylamino)ethoxy]aniline to generate the title compound. The 4-[2-(dimethylamino)ethoxy]aniline was prepared by treating commercial 4-aminophenol with DEAD, $\phi_3P$, and 2-(dimethylamino)ethanol in THF.

$^1$H NMR (300 MHz, $CD_3OD$), δ 2.16 (s,3H), 2.65–2.87 (m,2H), 2.90 (s,3H), 2.97 (s,6H), 3.60 (m,2H), 3.82 (s,3H), 4.33 (m,2H), 4.75–4.80 (m,1H), 6.85 (d, 1H), 7.01 (d,3H), 7.06 (d,2H), 7.28 (s,1H), 7.50 (dd,4H). Mass (M+H)=587. HPLC: 99.4% pure, retention time 11.84 minutes; protocol described in Example 1.

EXAMPLE 19

(R), (S)-α-[[2-Hydroxy-2-[4-hydroxy-3-[(methylsulfonyl)amino]phenyl]ethyl]amino]-4-methoxy-α-methyl-N-[3-[(dimethylamino)methyl]phenyl]benzeneacetamide, Trifluoroacetate

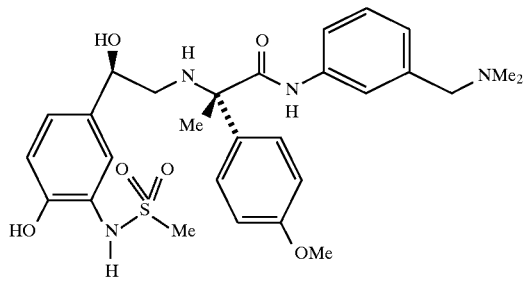

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]-amino]-4-methoxybenzeneacetic acid was condensed with 3-[(dimethylamino)methyl]aniline to generate the title compound. The 3-[(dimethylamino)methyl]aniline was prepared by treatment of commercial 3-nitrobenzoyl chloride with dimethylamine followed by sequential reduction with $SnCl_2$ in EtOAc at 20° C. for 18 hours and then $BH_3/THF$.

$^1$H NMR (400 MHz, $CD_3OD$): δ 7.63–7.52 (m, 4H), 7.36 (t, 1H), 7.26–7.21 (m, 2H), 7.06 (d, 2H), 7.00 (dd, 1H), 6.84 (d, 1H), 4.76 (dd, 1H), 3.92 (s, 2H), 3.82 (s, 3H), 2.90 (s, 3H), 2.79 (dd, 1H), 2.67 (dd, 1H), 2.49 (s, 3H), 2.48 (s, 3H), 2.18 (s, 3H). Mass Spec (ESI) (M+H)⁺=557. HPLC: Purity >76%; retention time=18.87 minutes; protocol described in Example 1.

EXAMPLE 20

(R), (S)-α-[[2-Hydroxy-2-[4-hydroxy-3-[(methylsulfonyl)amino]phenyl]ethyl]amino]-4-methoxy-α-methyl-N-[3-[(dimethylamino)sulfonyl]phenyl]benzeneacetamide, Trifluoroacetate

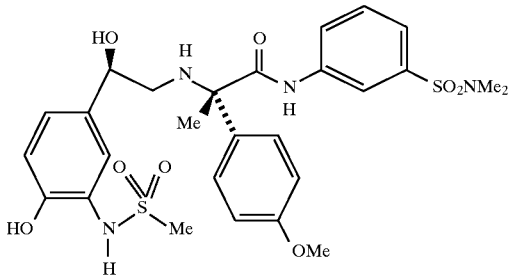

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]-amino]-4-methoxybenzeneacetic acid was condensed with 3-[(dimethylamino)sulfonyl]aniline to generate the title compound. The 3-[(dimethylamino)sulfonyl]aniline was prepared by sequential treatment of commercial 3-nitrobenzenesulfonyl chloride with Me₂NH in CH₂Cl₂ containing (i-Pr)₂NEt followed by reduction with SnCl₂ in EtOAc at 20° C.

$^1$H NMR (400 MHz, CD₃OD): δ 8.10 (d, 1H), 7.85–82 (m, 1H), 7.57–7.52 (m, 4H), 7.25 (d, 1H), 7.06 (d, 2H), 7.00 (dd, 1H), 6.84 (d, 1H), 4.76 (dd, 1H), 3.83 (s, 3H), 2.90 (s, 3H), 2.80 (dd, 1H), 2.69 (s, 6H), 2.64 (dd, 1H), 2.19 (s, 3H). Mass Spec (ESI) (M+H)⁺=607. HPLC: Purity >99%; retention time=17.47 min; protocol described in Example 1.

EXAMPLE 21

(R), (S)-[[3-[[2-[[2-Hydroxy-2-[4-hydroxy-3-[(methylsulfonyl)amino]phenyl]ethyl]amino]-2-(4-methoxyphenyl)-1-oxopropyl]amino]phenyl]methyl] phosphonic Acid, Diethyl Ester, Trifluoroacetate

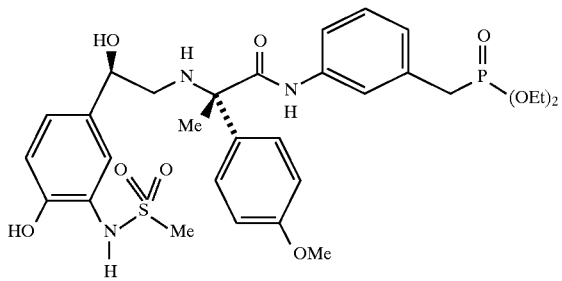

Following the procedure described in part E of Example 1 (R), (S)-α-[[2-[((1,1-dimethylethyl)dimethylsilyl)oxy]-2-[4-hydroxy-3-[(methylsulfonyl)amino]phenyl]ethyl]-amino]-4-methoxybenzeneacetic acid was condensed with diethyl 3-aminobenzylphosphonate to generate the title compound. The diethyl 3-aminobenzylphosphonate was prepared by sequential treatment of commercial 3-nitrobenzyl bromide with triethyl phosphite at 125° C. for 6 hours followed by reduction with Na₂S₂O₄ in THF/H₂O at 100° C.

$^1$H NMR (400 MHz, CD₃OD), δ 1.25 (t, 6H), 2.18 (s, 3H), 2.66 (dd, 1H), 2.80 (dd, 1H), 2.90 (s, 3H), 3.22 (d, 2H), 3.82 (s, 3H), 4.02 (q, 2H), 4.05 (q, 2H), 4.76 (dd, 1H), 6.83 (d, 1H), 6.99–7.12 (m, 4H), 7.25–7.32 (m, 2H), 7.44 (m, 1H), 7.49–7.57 (m, 3H). $^{13}$C NMR (100 MHz, CD₃OD) δ 16.7 (d), 19.3, 33.7 (d), 39.6, 51.0, 56.0, 63.8 (d), 68.9, 70.0, 114.0, 115.9, 116.6, 120.8, 123.6 (d), 124.4, 125.3, 126.1, 127.7 (d), 130.0, 130.6, 133.6 (d), 133.8, 139.1 (d), 151.6, 162.7, 170.6. Mass (M+H)=650. HPLC: 99.1% pure, retention time 20.2 minutes; protocol described in Example 1.

What is claimed is:

1. A compound of the formula

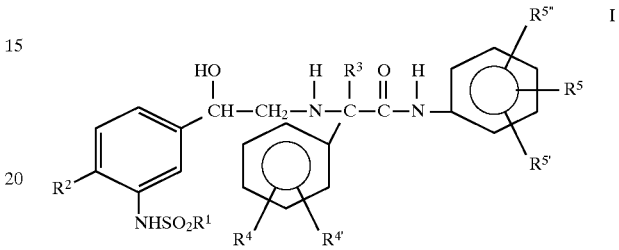

or pharmaceutically acceptable salts thereof wherein:

$R^1$ is lower alkyl, aryl or arylalkyl;

$R^2$ is hydrogen, hydroxyl, hydroxymethyl or halogen;

$R^3$ is hydrogen or alkyl;

$R^4$ and $R^{4'}$ are independently hydrogen, alkoxy, alkoxymethyl, hydroxyl, —CN, —CON($R^6$)$R^{6'}$, —CO₂$R^6$, —N($R^6$)$R^{6'}$, —NR⁶COR⁸, —NR⁶SO₂$R^1$; or $R^4$ and $R^{4'}$ may together with the carbon atoms to which they are bonded form a heterocycle;

$R^5$, $R^{5'}$ and $R^{5''}$ are independently A or B, wherein A is hydrogen, alkyl, cycloalkyl, halogen, hydroxyl, aryl, alkoxy, cyano, —SR⁷, —SOR⁷, —SO₂R⁷, —N($R^6$)$R^{6'}$, —NR⁶COR⁸, —OCH₂CON($R^6$)$R^{6'}$, —OCH₂CO₂$R^6$, CON($R^6$)$R^{6'}$, —CO₂$R^6$; and B is —(CH₂)$_m$PO(OR⁶)OR⁶', —O-aryl, —OCH₂CH₂N($R^6$)$R^{6'}$, —COR⁷, —SO₂N($R^6$)$R^{6'}$, —NR⁶CO₂R⁷, —NR⁶CO(N($R^6$)$R^{6'}$), heterocycle or —R⁵ and $R^{5'}$ may together with the carbon atoms to which they are bonded form a heterocycle; provided that at least one of $R^5$, $R^{5'}$ and $R^{5''}$ is B;

$R^6$ and $R^{6'}$ are independently hydrogen or lower alkyl;

$R^7$ is lower alkyl;

$R^8$ is hydrogen, lower alkyl, aryl or arylalkyl;

m is an integer of 0 to 6.

2. The compounds as recited in claim 1 wherein $R^1$ is lower alkyl, $R^2$ is hydroxyl, $R^3$ is lower alkyl and $R^4$ is alkoxy.

3. The compounds as recited in claim 1 wherein one of $R^5$, $R^{5'}$ and $R^{5''}$ is —(CH₂)$_m$PO(OR⁶)OR⁶'.

4. The compounds as recited in claim 1 wherein one of $R^5$, $R^{5'}$ and $R^{5''}$ is —(CH₂)$_m$PO(OR⁶)OR⁶', m is the integer 1 and the others are hydrogen.

5. The compounds as recited in claim 1 wherein $R^1$ is a lower alkyl;

$R^2$ is hydroxyl;

$R^3$ is a lower alkyl;

$R^4$ is alkoxy; and one of $R^5$, $R^{5'}$ and $R^{5''}$ is —(CH₂)$_m$PO(OR⁶)OR⁶'.

6. The compounds as recited in claim 1 wherein $R^1$ is lower alkyl;

$R^2$ is hydroxyl;

$R^3$ is lower alkyl;

$R^4$ is alkoxy; and $R^5$, $R^{5'}$ and $R^{5''}$ are independently alkoxy.

7. The compounds as recited in claim 1 wherein
$R^1$ is unsubstituted lower alkyl;
$R^2$ is hydroxyl;
$R^3$ is unsubstituted lower alkyl;
$R^4$ is lower alkoxy; and one of $R^5$, $R^{5'}$ and $R^{5''}$ is —(CH$_2$)$_m$PO(OR$^6$)OR$^{6'}$.

8. The compound as recited in claim 1, which is (R), (S)-[[4-[[2-[[2-hydroxy-2-[4-hydroxy-3-[(methylsulfonyl)amino]phenyl]ethyl]amino]-2-(4-methoxyphenyl)-1-oxopropyl]amino]phenyl]methyl]phosphonic acid, diethyl ester, trifluoroacetate;

(R), (S)-α-[[2-hydroxy-2-[4-hydroxy-3-[(methylsulfonyl)amino]phenyl]ethyl]amino]-4-methoxy-α-methyl-N-(3-phenoxyphenyl)benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[4-(2-oxazolyl)phenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[3-(2-oxazolyl)phenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[4-(2-thiazolyl)phenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[3-(2-thiazolyl)phenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[3-chloro-4-(2-thiazolyl)phenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[3-chloro-4-(2-oxazolyl)phenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[3-(2-oxazolyl)-4-chlorophenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-(3-acetylphenyl)benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-(3-aminosulfonylphenyl)benzeneacetamide;

(R), (S)-α-[[2-hydroxy-2-[4-hydroxy-3-[(methylsulfonyl)amino]phenyl]ethyl]amino]-4-methoxy-α-methyl-N-[(3-[[(propylamino)carbonyl]amino]phenyl)-benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[(4-[[(propylamino)carbonyl]amino]phenyl)-benzeneacetamide, trifluoroacetate;

(R), (S)-[3-[[2-[[2-hydroxy-2-[4-hydroxy-3-[(methylsulfonyl)amino]phenyl]ethyl]amino]-2-(4-methoxyphenyl)-1-oxopropyl]amino]phenyl)]carbamic acid, propyl ester, trifluoroacetate;

(R), (S)-α-[[2-hydroxy-2-[4-hydroxy-3-[(methylsulfonyl)amino]phenyl]ethyl]amino]-4-methoxy-α-methyl-N-(3-aminosulfonyl-4-chlorophenyl)benzeneacetamide;

(R), (S)-[[4-[[2-[[2-hydroxy-2-[4-hydroxy-3-[(methylsulfonyl)amino]phenyl]ethyl]amino]-2-(4-methoxyphenyl)-1-oxopropyl]amino]-3-chlorophenyl]methyl]phosphonic acid, diethyl ester, trifluoroacetate;

(R), (S)-α-[[2-hydroxy-2-[4-hydroxy-3-[(methylsulfonyl)amino]phenyl]ethyl]amino]-4-methoxy-α-methyl-N-[3-[2-(dimethylamino)ethoxy]phenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[4-[2-(dimethylamino)ethoxy]phenyl]benzeneacetamide, trifluoroacetate;

(R), (S)-α-[[2-hydroxy-2-[4-hydroxy-3-[(methylsulfonyl)amino]phenyl]ethyl]amino]-4-methoxy-α-methyl-N-[3-[(dimethylamino)sulfonyl]phenyl]benzeneacetamide, trifluoroacetate;

(R), (S)-[[3-[[2-[[2-hydroxy-2-[4-hydroxy-3-[(methylsulfonyl)amino]phenyl]ethyl]amino]-2-(4-methoxyphenyl)-1-oxopropyl]amino]phenyl]methyl]phosphonic acid, diethyl ester, trifluoroacetate; or a pharmaceutically acceptable salt thereof.

9. The compound as recited in claim 1, which is (R),(S)-[[4-[[2-[[2-hydroxy-2-[4-hydroxy-3-[(methylsulfonyl)amino]phenyl]ethyl]amino]-2-(4-methoxyphenyl)-1-oxopropyl]amino]phenyl]methyl]phosphonic acid, diethyl ester, trifluoroacetate or a pharmaceutically acceptable salt thereof.

10. A pharmaceutical composition comprising a compound of claim 1 and a pharmaceutically acceptable carrier.

11. A method for treating diabetes comprising administering to a mammalian specie in need thereof a therapeutically effective amount of a composition of claim 10.

12. A method for treating obesity comprising administering to a mammalian specie in need thereof a therapeutically effective amount of a composition of claim 10.

13. A method for treating intestinal hypermotility comprising administering to a mammalian specie in need thereof a therapeutically effective amount of a composition of claim 10.

14. A pharmaceutical composition comprising a compound of claim 1 in combination with a beta$_1$ or beta$_2$ adrenergic blocker or stimulant and a pharmaceutically acceptable carrier.

15. A method for treating diabetes comprising administering to a mammalian specie in need thereof a therapeutically effective amount of a composition of claim 14.

16. A method for treating obesity comprising administering to a mammalian specie in need thereof a therapeutically effective amount of a composition of claim 14.

17. A method for treating gastrointestinal diseases comprising administering to a mammalian specie in need thereof a therapeutically effective amount of a composition of claim 14.

18. A pharmaceutical composition comprising a compound of claim 1 in combination with a centrally or systemically active agent which reduces food intake and a pharmaceutically acceptable carrier.

19. The pharmaceutical composition as recited in claim 18 wherein the centrally or systemically active agent which reduces food intake is leptin.

20. A method for treating diabetes comprising administering to a mammalian specie in need thereof a therapeutically effective amount of a composition of claim 18.

21. A method for treating obesity comprising administering to a mammalian specie in need thereof a therapeutically effective amount of a composition of claim 18.

22. A method for treating gastrointestinal diseases comprising administering to a mammalian specie in need thereof a therapeutically effective amount of a composition of claim 18.

23. A compound of the formula

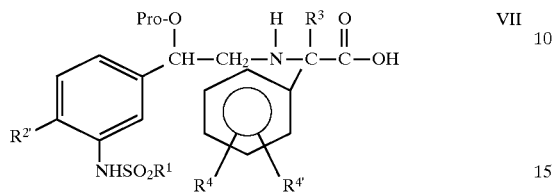

where

Pro is a protecting group;

$R^1$ is lower alkyl, aryl or arylalkyl;

$R^{2'}$ is hydrogen, hydroxyl, halogen, —$CO_2R^7$, —$CH_2OPro'$, or —O-Pro', where Pro' is a protecting group;

$R^3$ is hydrogen or alkyl;

$R^4$ and $R^{4'}$ are independently hydrogen, alkoxy, hydroxyl, alkoxymethyl, —CN, —$CON(R^6)R^{6'}$, —$CO_2R^7$, —$N(R^6)R^{6'}$, —$NR^6COR^8$, —$NR^6SO_2R^1$; or $R^4$ and $R^{4'}$ may together with the carbon atoms to which they are bonded form a heterocycle;

$R^6$ and $R^{6'}$ are independently hydrogen or lower alkyl;

$R^7$ is lower alkyl; and $R^8$ is hydrogen, lower alkyl, aryl or arylalkyl.

* * * * *